United States Patent [19]
Oshlack et al.

[11] Patent Number: 5,356,467
[45] Date of Patent: Oct. 18, 1994

[54] CONTROLLED RELEASE COATINGS DERIVED FROM AQUEOUS DISPERSIONS OF ZEIN

[75] Inventors: Benjamin Oshlack, New York, N.Y.; James McGinity, Austin, Tex.; Mark Chasin, Manalapan, N.J.; Roland Bodmeier, Austin, Tex.

[73] Assignee: Euroceltique S.A., Luxembourg, Luxembourg

[21] Appl. No.: 103,887

[22] Filed: Aug. 6, 1993

Related U.S. Application Data

[63] Continuation-in-part of Ser. No. 930,107, Aug. 13, 1992.

[51] Int. Cl.$^5$ ............................................... C08L 89/00
[52] U.S. Cl. .................................... 106/153; 530/373; 252/174.13; 512/4; 71/64.11; 424/457; 424/468
[58] Field of Search ..................... 530/373; 106/153; 252/174.13; 512/4; 71/64.11; 424/457, 468

[56] References Cited

U.S. PATENT DOCUMENTS

| | | | |
|---|---|---|---|
| 2,377,237 | 5/1945 | James | 106/153 |
| 2,676,169 | 4/1954 | Baldoni | 260/123 |
| 2,772,488 | 2/1942 | Swallen | 106/153 |
| 2,791,509 | 5/1957 | Cosler | 99/166 |
| 3,365,365 | 1/1968 | Butler et al. | 167/82 |
| 3,370,054 | 2/1968 | Loew | 260/123 |
| 3,371,015 | 2/1968 | Sjogren et al. | 167/82 |
| 4,931,295 | 6/1990 | Courtright et al. | 426/5 |
| 4,983,403 | 1/1991 | Ardaillon et al. | 426/2 |

OTHER PUBLICATIONS

Swallen, "Zein", *Industrial and Engineering Chemistry*, pp. 394–398, Mar., 1941.

Manley, et al. "Binary Solvents for Zein", *Industrial and Engineering Chemistry*, pp. 661–665, Jun., 1943.

*Primary Examiner*—David Brunsman
*Attorney, Agent, or Firm*—Steinberg, Raskin & Davidson

[57] ABSTRACT

Stable aqueous dispersions of zein which may be used as controlled release coatings of pharmaceutical, animal, health, or food products in an inorganic solvent-free environment are disclosed, as well as methods for preparing the same.

34 Claims, 8 Drawing Sheets

CONTROLLED RELEASE COATINGS DERIVED FROM AQUEOUS DISPERSIONS OF ZEIN

This application is a continuation-in-part of U.S. application Ser. No. 07/930,107, filed Aug. 13, 1992 pending.

BACKGROUND OF THE INVENTION

Coatings have long been applied to pharmaceuticals, animal health products, and food products for various reasons, including masking unpleasant taste, protecting components from degradation, controlling the site of drug release (enteric coating), controlling the absorption of the drug compound by retarding release of the drug from the dosage form, improving the appearance of the product, and changing the physical surface characteristics of the ingredients.

The oldest method of coating is perhaps sugar-coating. In sugar coating, the objects to be coated are moistened with an aqueous sugar solution and tumbled (for example in a rotating pan), and then dried. The moistening and drying procedures are generally repeated many times before satisfactory protection of the object to be coated and a smooth surface are obtained.

It is generally considered desirable to apply a seal coat directly over the uncoated tablet, etc. in order to separate the object to be coated from the water that is used in the coating process. Many substances have been used as sealing agents in this step, including cellulose-acetate-phthalate, zein, shellac, and other specific resins. Thereafter, the product may be subcoated, syrup coated, finished, and polished, although many variations of these procedures are used. The sealing coat is applied as a dilute, nonaqueous solution, and not more than two or three thin coats are used to seal the tablets.

More recently, film-coating techniques that have used a wide variety of materials of coating agents have been developed, in order to overcome the host of problems that can be encountered in attempting to sugar coat a tablet, such as color spotting, cracking of the coating, degradation of the drug in the tablet, and excessive subcoatings which cause retardation of disintegration and bioavailability.

Most film-coats are prepared by depositing one or more film-forming polymers onto the object to be coated, resulting in coatings that represent usually from about 2 to 10% by weight of the coated tablet. Such film coatings tend to have better resistance to chipping of the coating, increased tablet strength, and decreased production cost as compared to sugar coating. The polymers used in film-coating are generally water soluble or water dispersible cellulose derivatives such as hydroxypropyl methylcellulose and carboxymethylcellulose.

Hydrophobic polymers such as certain cellulose derivatives, acrylic resins, waxes, higher aliphatic alcohols, and polylactic polyglycolic acids have been used in the development of controlled release pharmaceutical dosage forms, such as tablets, capsules, suppositories, spheroids, beads or microspheres by, e.g., overcoating the individual dosage units with these hydrophobic polymers.

It is known in the prior art that these hydrophobic coatings can be applied either from a solution, suspension or as dry powders. Since most of these polymers have a low solubility in water, they are usually applied by dissolving the polymer in an organic solvent and spraying the solution onto the individual drug forms (such as beads or tablets) and evaporating off the solvent.

The use of organic solvents in the preparation of polymer coatings is considered problematic as the formulations have inherent problems with regard to flammability, carcinogenicity, and safety in general. In addition, the use of organic solvents is not favored due to environmental concerns.

Most commercially available aqueous dispersions of pre-formed polymers (e.g., ethylcellulose-Aquacoat ®, Surelease ®) are prepared via emulsification of organic polymer solutions or polymer melts into an aqueous phase followed by homogenization. Organic solvents used in this process are water-immiscible.

While coatings for pharmaceutical formulations, etc., comprising zein are considered desirable, the use of such coatings has been limited because zein is not soluble in water-immiscible organic solvents and therefore cannot be prepared by the traditional emulsification techniques described above.

With regard to confectionery coatings, U.S. Pat. No. 2,791,509 (Cosler) describes a coating for non-cereal confectionery articles which comprises zein and acetylated glycerides which are applied to the food articles in an edible organic solvent vehicle, such as 90% ethanol, or ethanol denatured with a minor amount of ethyl acetate. However, it is stated therein that virtually any organic solvent can be used which is edible, nontoxic, and in which the zein and acetylated monoglyceride are soluble. The coating is said to form a continuous barrier against the penetration of water into the confectionery and against penetration of fat, oil and moisture from the interior of the confectionery to the outside.

U.S. Pat. No. 4,931,295 (Courtright, et al.) is related to methods for producing a chewing gum with a zein coated "delayed release" high-potency sweetener. The term "delayed release" as used therein is intended to infer a delayed release of the high-potency sweetener during chewing of the gum and during storage. In this process, the zein is mixed with a solvent for the zein, and a water soluble modified cellulose compound such as HPMC to form a modified zein solution. This modified zein solution is applied to a high-potency sweetener and then dried to produce the delayed release sweetener particles. The particles are then added to a chewing gum formulation. In a preferred embodiment, the zein is dissolved in water having a pH of between about 11.5 and about 12.1 and contains about 13 weight percent zein. Thee zein is said to be either completely dissolved or a major portion of the zein is dissolved and a minor portion is suspended in the water. In a second preferred method, the zein is dissolved in ethanol, to between about 10-15% by weight of the solution. The zein is said to comprise about 1-15% of the coated high-potency sweetener, the zein, and the HPMC.

U.S. Pat. No. 3,371,015 (Sjogren, et al.) describes tablet coatings comprising an inner layer of a polyethylene glycol which is soluble in water and in certain organic solvents, and an outer layer of a film-forming thermoplastic substance which is water-insoluble but soluble in volatile organic solvents. Substances which are considered to be suitable for the ]outer layer include cellulose acetates, acrylic resins, silicone resins, as well as shellac and zein.

U.S. Pat. No. 3,365,365 (Butler, et al.) describes pharmaceutical compositions in the form of beadlets suitable for filling into hard shell capsules, wherein the beadlets are enteric coated with a coating containing zein and an abietic acid type rosin. The enteric coating which is used for preparing chlordiazepoxide beadlets are produced by mixing the abietic acid type rosin with zein, a wetting agent, an anhydrous lower aliphatic alcohol, and a plasticizer.

U.S. Pat. No. 3,370,054 (Loew) describes deaminated zein dispersible in solutions having a pH of at least 6.5 which is prepared by hydrolyzing zein with strong alkalies, and thereafter removing the alkali by precipitation.

U.S. Pat. No. 4,983,403 (Ardaillon, et al.) describes a biologically active substance for the feeding of ruminants. The composition consists of a ruminant feed additive coated with a mixture consisting of zein in combination with a non-water-soluble polymer; a hydrophobic substance; a non-water-soluble polymer and a plasticizing agent; or a hydrophobic substance and a non-water-soluble polymer. The coating mixture is said to be obtained by dispersing or dissolving zein in a solution or dispersion of the non-water-soluble polymer and/or of the hydrophobic substance, and optionally, the plasticizing agent, in an organic solvent or in a mixture of suitable organic solvents. The coating mixture is obtained after evaporation of the solvent or solvents.

OBJECTS AND SUMMARY OF THE INVENTION

It is therefore an object of the present invention to prepare aqueous dispersions of zein to be used in the coating of pharmaceutical, animal, health, or food products in an organic solvent-free environment.

It is a further object of the present invention to prepare a solid powder of zein in a redispersible form which thereafter may then be dispersed by the consumer prior to the coating process.

It is a further object of the present invention to provide a stable aqueous dispersion of zein which may be stored, e.g., at room temperature, for an extended period of time.

It is a further object of the present invention to provide a controlled release coating of an aqueous dispersion of zein for a substrate comprising an active agent, such as a tablet core, which coating provides a controlled release of the active agent at a desired rate when the coated substrate is exposed to aqueous solution.

It is a further object of the present invention to provide a method for obtaining a controlled release coating of an aqueous dispersion of zein for coating a substrate comprising an active agent, which coating provides a reproducible controlled release of the active agent at a desired rate when the coated substrate is exposed to an aqueous solution.

In view of the above objects and others, the present invention is related to an aqueous dispersion of zein, the aqueous dispersion comprising from about 0.1 to about 10 percent zein. The aqueous dispersions of the present invention preferably have a pH from about 4 to about 6. Generally, the particle size of the zein in the aqueous dispersion is from about 0.01 to about 10 $\mu$m. The aqueous dispersion is essentially free of organic solvents.

The present invention is also related to a method for preparing an aqueous dispersion of zein, wherein a solvent mixture comprising water and from about 60 to about 90 percent of an organic solvent is prepared, zein is added to the solvent mixture in such a proportion to the solvent mixture that the zein dissolves in the solvent mixture, and the zein is precipitated as fine particles to obtain an aqueous dispersion comprising from about 0.1 to about 10 percent w/v of zein. The organic solvent may be, e.g., ethanol, acetone, and mixtures thereof.

In a preferred embodiment, the method further comprises the steps of pouring the solution of zein as a thin stream into an aqueous phase under continuous stirring to thereby precipitate the zein as fine particles. The organic solvent is then evaporated from the mixture, and the resulting aqueous phase is concentrated to a zein concentration from about 0 1 to about 10% w/v.

The present invention is also related to a powdered, redispersible form of zein. This zein powder may be redispersed prior to use in a coating process.

In further embodiments, the present invention is related to a stabilized aqueous dispersion of zein comprising from about 0.1 to about 10 percent zein w/v having a particle size from about 0.01 $\mu$m to about 10 $\mu$m, and an effective amount of a pharmaceutically acceptable preservative in an amount effective to prevent sedimentation.

In preferred embodiments, the pharmaceutically acceptable preservative is preferably selected from the group consisting of benzalkonium chloride, benzoic acid, benzyl alcohol, methyl paraben, propyl paraben, ethyl paraben, butyl paraben, sorbic acid, a quaternary ammonium salt, phenol, cresol, mercury-containing preservatives, and mixtures of any of the foregoing.

Other further embodiments of the present invention are directed to a method of preparing a stable aqueous dispersion of zein, comprising adding a pharmaceutically acceptable preservative to an aqueous dispersion of zein comprising from about 0.1 to about 10 percent zein w/v in an amount effective to prevent sedimentation of the zein when said stabilized aqueous dispersion of zein.

In yet other embodiments, the present invention is directed to a solid controlled release formulation, such as a tablet, comprising a substrate comprising an active agent, said substrate coated with a controlled release coating to a weight gain from about 0.5 to about 100 percent, said controlled release coating comprising (i) an aqueous dispersion of from about 0.1 to about 10 percent zein w/v having a particle size from about 0.01 $\mu$m to about 10 $\mu$m, and preferably from about 0.1 $\mu$m to about 2 $\mu$m, said aqueous dispersion obtained by precipitating zein by pouring a solution of zein in a solvent comprising water and from about 60 to about 90 percent organic solvent as a thin stream into an aqueous phase under continuous stirring, the organic solvent thereafter being substantially removed and the resulting aqueous phase concentrated; (ii) a pharmaceutically acceptable preservative; (iii) a pharmaceutically acceptable plasticizer, the preservative and the plasticizer each being included in an amount necessary to provide a continuous film capable of releasing the active agent at a desired rate when the formulation is exposed to an aqueous solution.

The active agent may be, e.g., a systemically active therapeutic agent, a locally active therapeutic agent, a disinfecting and sanitizing agent, a cleansing agent, a fragrance agent and a fertilizing agent. Other applications for the controlled release formulations include agricultural, food and household products.

The controlled release coating of the present invention may further comprise a rate-controlling agent selected from the group consisting of water soluble hydrophilic polymers, semi-permeable polymers, selectively permeable polymers, pore-forming materials, microporous material, erosion promoting agents, and mixtures of any of the foregoing. Instead of or in addition to the rate-controlling agent, the controlled release coating may further comprise one or more release-modifying passageways formed therein.

The present invention is further related to a method for preparing a controlled release formulation Comprising coating a substrate comprising an active agent with a Sufficient amount of the preserved, plasticized aqueous dispersion of zein of the present invention to obtain a predetermined Controlled release of the active agent when the coated substrate is exposed to aqueous solutions.

BRIEF DESCRIPTION OF THE DRAWINGS

The following drawings are illustrative of embodiments of the invention and are not meant to limit the scope of the invention as encompassed by the claims.

DETAILED DESCRIPTION

Figure 1:
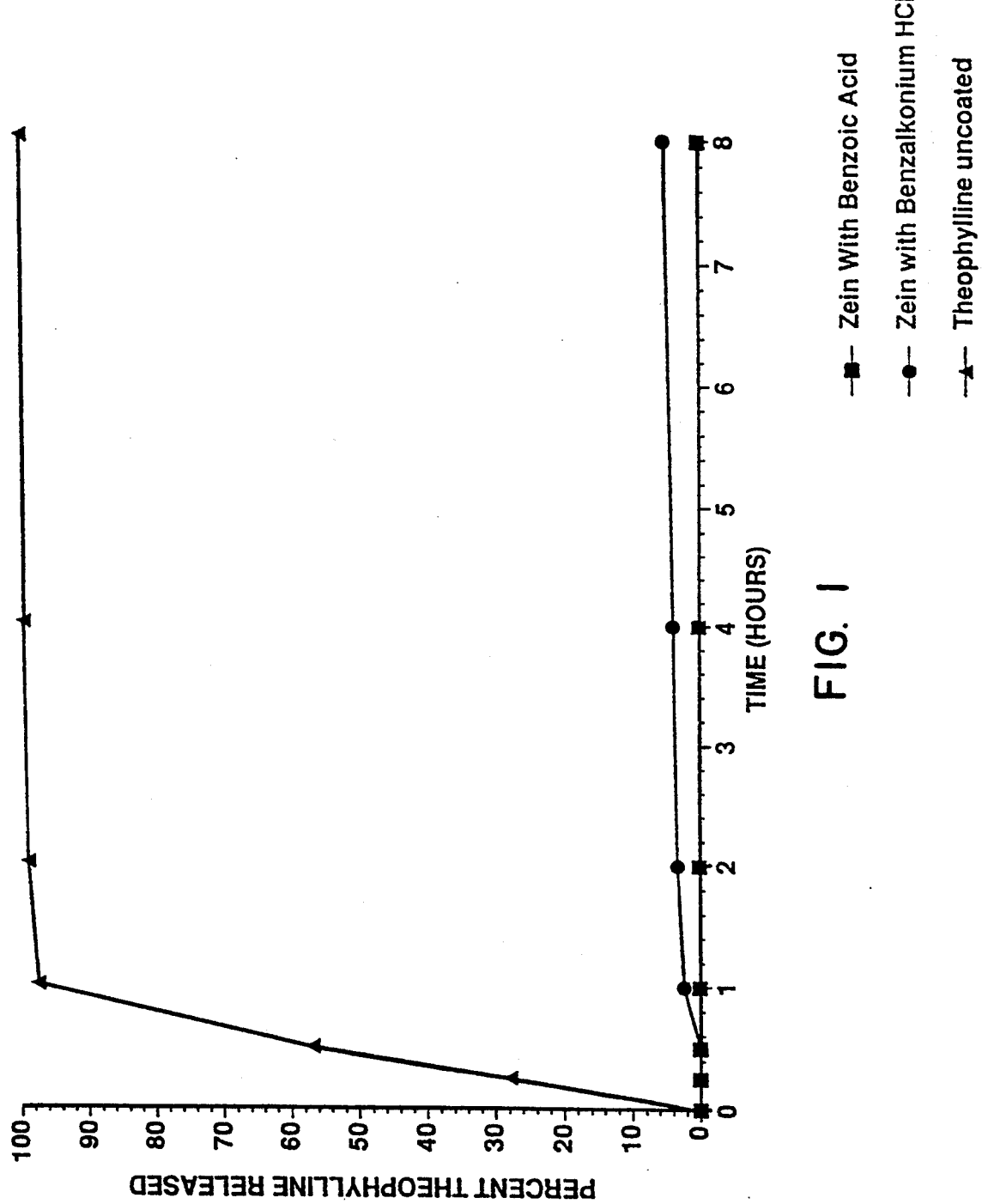
FIG. 1 is a graphical representation of the dissolution profiles obtained by Examples 29 and 30.

Zein is a protein of the prolamine class which is a fraction of a protein contained in corn. Commercially, it has been obtained, for example, by extracting corn gluten with a 60-80% isopropyl alcohol under alkaline conditions. After neutralization and concentration, the extract containing the zein is sprayed into cold water, causing the zein to precipitate. See, e.g., U.S. Pat. No. 2,676,169 (Baldoni) and the patents cited therein.

In the past, zein has found many uses as a coating material. However, the use of zein as a coating material has been considered problematic because zein does not bar the migration or transfer of moisture, and has been known to form a relatively hard coating having a low tensile strength and is easily fractured. As a coating material for food products, zein coatings are known to form relatively hard and crunchy coatings.

Zein is soluble in aqueous alcohols, glycols, and acetone/water mixtures. The preparation of zein dispersions is governed by the solubility properties of this natural polymer. Zein is not soluble in water-immiscible organic solvents (e.g., methylene chloride) which are commonly used to prepare pseudolatexes by emulsification techniques.

In accordance with preferred embodiment of the present invention, zein dispersions are prepared by dissolving zein in a mixture of water with either ethanol and/or acetone.

Preferably, in order to maximize the amount of zein in the dispersion, the solvent mixtures used in the present invention have a volume percentage of ethanol, acetone or mixtures thereof from about 60 to about 90 percent. However, it is possible to obtain an aqueous dispersion according to the present invention with a lower amount of the organic solvent.

Instead of ethanol and/or acetone, other organic solvent/water systems may be used to dissolve the zein. For example, the solvent mixtures of the present invention may comprise isopropanol, methanol, and the like. Isopropanol and/or methanol in a ratio of 7:3 (organic solvent/water) work up to a zein concentration of about 10% zein w/v. At higher percentages (e.g., 15% zein w/v) a gel is formed. Other solvent systems, such as ethyl acetate, DMF and DMSO may also work but have undesirable properties relative to the preferred embodiments wherein the organic solvent comprises ethanol/water and/or acetone/water.

It has been discovered that more than i40% w/v zein can be dissolved in solvent mixtures with a volume percentage of ethanol and/or acetone between from about 60 to about 90. The viscosity of these concentrated solutions is relatively high.

In a preferred embodiment of the invention, the solution of zein is added to an agitated aqueous phase. Zein precipitates as fine particles resulting in a dispersion. These dispersions are then preferably concentrated, e.g., by evaporating water.

The upper limit of zein in the zein dispersions of the present invention are zein concentrations of about 10% w/v. Higher concentrations have been found to result in the formation of agglomerates. After concentrating the dispersions of the present invention, it has been found that the maximum solids content obtainable is about 10% w/v. Agglomeration and sticking to the vessel are observed at higher solids content.

The pH of the aqueous zein dispersions of the present invention is generally in the range from about pH 3 to about 7. In preferred embodiments of the present invention, the zein concentration in the aqueous dispersion is from about 6 to about 10% w/v, and the pH is from about 4 to about 6. In most preferred embodiments, the aqueous zein dispersion has a pH from about 4.5 to about 5.5. When the pH of an aqueous zein dispersion of 6-10% w/v is adjusted substantially above pH 6 or below pH 4 via the use of electrolytes or buffers, the dispersion has been found to become unstable and a fine dispersion of zein is no longer obtained which would be suitable for commercial applications, such as in spray coatings. For example, at least a portion of the zein particles will no longer be in a desirable nanoparticle size range. The zein in the dispersion may precipitate, agglomerate, and/or flocculate at such pH levels. Stability may be achieved at substantially higher pH's, e.g. pH 9-10 or above. As indicated in the Merck Index, zein is soluble in alkaline solutions of pH 11.5 or greater. Therefore, it is possible at pH 9-10 and above, a portion of the zein in the aqueous dispersion is solubilized.

If an adjustment of the pH of the aqueous dispersion is deemed desirable, it may be possible to do so via the use of an inorganic or organic monomeric or polymeric acidic or basic compound which do not ionize to any substantial degree without causing precipitation, agglomeration and/or flocculation in the aqueous pseudolatex dispersion.

In another embodiment of the present invention, the pH of the aqueous zein dispersion can be adjusted by adding a suitable buffer system to adjust the pH of the aqueous zein dispersion to above about pH 9. For example, suitable buffer systems include an ammonium carbonate-ammonia buffer, a citric acid-sodium phosphate buffer, and a boric acid-potassium chloride-sodium hydroxide buffer.

In a preferred embodiment, the particle size of the zein in the aqueous dispersion is from about 0.01 to about 10 μm, although depending upon the desired use of the end product, larger particle sizes may be acceptable. In most preferred embodiments of the present invention, the majority of the zein particles in the resultant aqueous dispersion are from about 100 to about 300 nanometers.

In another embodiment of the present invention, a zein dispersion is prepared as set forth above and then is dried to obtain fine particles, preferably smaller than about 10μm. The fine particles of zein which are obtained are preferably in the size range from about 0.1 to about 5.0 μm. The zein dispersion may be dried by any suitable method known to those skilled in the art, such as spray drying, freeze drying, Oven drying, vacuum drying, etc. The zein powder may thereafter be redispersed in an aqueous solution when so desired.

The use of a redispersible zein powder is desirable for a variety of reasons. First, microbiological concerns and the necessary addition of preservatives to the aqueous dispersion would be minimized or eliminated. Secondly, the redispersible zein powder of the present invention results in reduced shipping volumes and a greater flexibility at the formulation stage.

The aqueous dispersions of zein used as coatings in the present invention may be used in virtually any application in which a coating would be desirable, including use in conjunction with food products, animal health products, confectionery products, and various pharmaceuticals, including tablets, spheroids, granules (or beads), microspheres, seeds, pellets, ion-exchange resin beads, and other multi-particulate systems in order to obtain a desired controlled release of the therapeutically active agent. Granules, spheroids, or pellets, etc., prepared in accordance with the present invention can be presented in a capsule or in any other suitable dosage form.

The coating formulations of the present invention should be capable of producing a continuous film that is smooth and elegant, capable of supporting pigments and other coating additives, non-toxic, inert, and tack-free. To achieve this objective, other suitable pharmaceutically acceptable agents may be added to the dispersion. For example, the inclusion of a plasticizer may be desirable in the event that the film formed by the zein coating is otherwise too brittle. The addition of a surfactant may also be desirable. Water-soluble plasticizers, e.g., glycerin, propylene glycol, and polyethylene glycol (e.g., PEG 400), are preferred in comparison to the water-insoluble plasticizers, e.g., dibutyl sebacate (DBS), triethyl citrate (TEC; sometimes classified as a water-soluble plasticizer), tributyl citrate (TBC), acetyltributyl citrate (ATBC), and acetyltriethyl citrate (ATEC). Propylene glycol at a concentration from about 20 to about 25%, based on the amount of zein, appears to be the best plasticizer. Certain plasticizing agents, such as polypropylene glycol and polyethylene glycol, have been found to solubilize part of the protein (zein) as well as plasticize the film. The resultant product therefore comprises a solution of zein as well as a dispersion of zein.

In preferred embodiments, the plasticizer is water-soluble and is incorporated in a sufficient amount to provide a desired formation of the film to be made from the aqueous zein dispersion of the present invention.

The amount of plasticizer added is preferably from about 20 to about 40 percent, based on the zein content.

One skilled in the art will recognize that the selection of such additional pharmaceutical agents and the level of inclusion of these agents in the zein latex should be optimized for the particular use. Also, in the case of pharmaceutical coatings, once the beads, tablets, etc. have been successfully coated, the dissolution properties of the particular formulation can be optimized.

Controlled release coatings obtained from the aqueous dispersions of the present invention have been determined to fail relatively quickly, i.e., the active agent comprising the substrate is released very quickly due to failure of the film coat. Upon inspection, it was been discovered that the coating had numerous small cracks which allowed rapid hydration of the tablet core. The cause of this rapid disintegration of the continuity of the film coating is not known.

However, in a further embodiment of the present invention, it has now been surprisingly discovered that the addition of a pharmaceutically acceptable preservative prevents the degradation of the zein dispersion of the present invention. As previously mentioned, it is therefore desired in certain embodiments of the present invention to include a pharmaceutically acceptable preservative is selected from the group consisting of benzalkonium chloride, benzoic acid, benzyl alcohol, methyl paraben, propyl paraben, ethyl paraben, butyl paraben, sorbic acid, a quaternary ammonium salt, phenol, cresol, mercury-containing preservatives, and mixtures of any of the foregoing.

With regard to the aqueous dispersions of the present invention, the pharmaceutically acceptable preservative is included in an amount effective to prevent sedimentation of the zein (e.g., less than about 20% sedimentation after 30 days). In embodiments of the present invention which are directed to controlled release coatings, the preservative is included in an amount which is effective to provide a continuous film capable of releasing the active agent at a desired rate when the formulation is exposed to an aqueous solution.

In certain preferred embodiments, methyl paraben in an amount of at least 0.05%, w/v is incorporated into the aqueous dispersion of zein. In another preferred embodiment, methyl paraben and propyl paraben in a ratio of about 10:1 are incorporated into the aqueous dispersion of zein, the methyl paraben being present in an amount of at least 0.05%, w/v In an especially preferred embodiment, the preservative comprises about 0.2% methyl paraben and about 0.02% propyl paraben, w/v.

The release of the active agent from the controlled release formulation of the present invention can be further influenced, i.e., adjusted to a desired rate, by the addition of one or more pore-formers which can be inorganic or organic, and include materials that can be dissolved, extracted or leached from the coating in the environment of use. Upon exposure to fluids in the environment of use, the pore-formers are, e.g., dissolved, and channels and pores are formed that fill with the environmental fluid.

For example, the pore-formers may comprise one or more water-soluble hydrophilic polymers in order to modify the release characteristics of the formulation. Examples of suitable hydrophilic polymers include hydroxypropylmethylcellulose, cellulose ethers and protein-derived materials. Of these polymers, the cellulose ethers, especially hydroxyalkylcelluloses and carboxyalkylcelluloses, are preferred. Also, synthetic water-soluble polymers may be used, such as polyvinylpyrrolidone, cross-linked polyvinylpyrrolidone, polyethylene oxide, etc., water-soluble polydextrose, saccharides and polysaccharides, such as pullulan, dextran, sucrose, glucose, fructose, mannitol, lactose, mannose, galactose, sorbitol and the like In certain preferred embodiments of the present invention, the hydrophilic polymer comprises hydroxypropylmethylcellulose.

Other examples of pore-formers include alkali metal salts such as lithium carbonate, sodium chloride, sodium bromide, potassium chloride, potassium sulfate, potassium phosphate, sodium acetate, sodium citrate, and the like. The pore-forming solids may also be polymers which are soluble in the environment of use, such as Carbowaxes®, Carbopol®, and the like The pore-formers embrace diols, polyols, polyhydric alcohols, polyalkylene glycols, polyglycols, poly-alkylenediols, and the like.

Semipermeable polymers may also be incorporated in the controlled release coating as a pore-former to change the release characteristics of the formulation. Such semipermeable polymers include, for example, cellulose acylates, acetates, and other semipermeable polymers such as those described in U.S. Pat. No. 4,285,987 (hereby incorporated by reference), as well as the selectively permeable polymers formed by the co-precipitation of a polycation and a polyanion as disclosed in U.S. Pat. Nos. 3,173,876; 3,276,586; 3,541,005; 3,541,006 and 3,546,142 (hereby incorporated by reference).

Other pore-formers which may be useful in the formulations of the present invention include starch, modified starch, and starch derivatives, gums, including but not limited to xanthan gum, alginic acid, other alginates, bentonite, veegum, agar, guar, locust bean gum, gum arabic, quince psyllium, flax seed, okra gum, arabinogalactin, pectin, tragacanth, scleroglucan, dextran, amylose, amylopectin, dextrin, etc., cross-linked polyvinylpyrrolidone, ion-exchange resins, such as potassium polymethacrylate, carrageenan, kappa-carrageenan, lambdacarrageenan, gum karaya, biosynthetic gum, etc. Other pore-formers include materials useful for making microporous lamina in the environment of use, such as polycarbonates comprised of linear polyesters of carbonic acid in which carbonate groups reoccur in the polymer chain, microporous materials such as bisphenol, a microporous poly(vinylchloride), microporous polyamides, microporous modacrylic copolymers, microporous styrene-acrylic and its copolymers, porous polysulfones, halogenated poly(vinylidene), polychloroethers, acetal polymers, polyesters prepared by esterification of a dicarboxylic acid or anhydride with an alkylene polyol, poly(alkylenesulfides), phenolics, polyesters, asymmetric porous polymers, cross-linked olefin polymers, hydrophilic microporous homopolymers, copolymers or interpolymers having a reduced bulk density, and other similar materials, poly(urethane), cross-linked chain-extended poly(urethane), poly(imides), poly(benzimidazoles), regenerated proteins, semi-solid cross-linked poly(vinylpyrrolidone).

In general, the amount of pore-former included in the controlled release coatings of the present invention may be from about 0.1% to about 80%, by weight relative to the combined weight of hydrophobic acrylic polymer and pore-former.

The controlled release coatings of the present invention may also include an exit means comprising at least one passageway, orifice, or the like. The passageway may be formed by such methods as those disclosed in U.S. Pat. Nos. 3,845,770; 3,916,889; 4,063,064; and 4,088,864 (all of which are hereby incorporated by reference). The passageway can have any shape such as round, triangular, square, elliptical, irregular, etc. The passageway may be included instead of, or in addition to, the inclusion of permeability-enhancing compounds, hydrophilic monomers, pH-sensitive polymers, and/or pore-formers, in order to obtain a release of the active agent(s) included in the formulation.

A wide variety of therapeutically active agents can be used in conjunction with the present invention. The therapeutically active agents (e.g. pharmaceutical agents) which may be used in the compositions of the present invention include both water soluble and water insoluble drugs. Examples of such therapeutically active agents include antihistamines (e.g., dimenhydrinate, diphenhydramine, chlorpheniramine and dexchlorpheniramine maleate), analgesics (e.g., aspirin, codeine, morphine, dihydromorphone, oxycodone, etc.), anti-inflammatory agents (e.g., naproxyn, diclofenac, indomethacin, ibuprofen, acetaminophen, aspirin, sulindac), gastro-intestinals and anti-emetics (e.g., metoclopramide), anti-epileptics (e.g., phenytoin, meprobamate and nitrezepam), vasodilators (e.g., nifedipine, papaverine, diltiazem and nicardirine), anti-tussive agents and expectorants (e.g., codeine phosphate), anti-asthmatics (e.g. theophylline), anti-spasmodics (e.g. atropine, scopolamine), hormones (e.g., insulin, leparin), diuretics (e.g., eltacrymic acid, bendrofluazide), anti-hypotensives (e.g., propranolol, clonidine), bronchodilators (e.g., albuterol), anti-inflammatory steroids (e.g., hydrocortisone, triamcinolone, prednisone), antibiotics (e.g., tetracycline), antivirals, antihemorrhoidals, hypnotics, psychotropics, anti-diarrheals, mucolytics, sedatives, decongestants, laxatives, antacids, vitamins, stimulants (including appetite suppressants such as phenylpropanolamine). The above list is not meant to be exclusive.

In another preferred embodiment of the present invention, the active agent is disinfecting agent, e.g. chlorine compound, calcium hypochlorite and the aqueous solution is an environment of use, e.g., a surrounding body of water such as a recreational pool.

In still another preferred embodiment of the present invention, the active agent is a cleansing agent, e.g., germicides, deodorants, surfactants, fragrances, perfumes, sanitizers, dye and the environment of use is an aqueous solution, e.g. a urinal or toilet bowl.

In yet another preferred embodiment of the present invention, the active agent is a chemical impregnant, e.g., fertilizer, animal repellents, pesticides, herbicides, fungicides, plant growth stimulants, and the environment of use is anywhere around the home, e.g. soil, trees etc.

DETAILED DESCRIPTION OF THE PREFERRED EMBODIMENTS

The following examples illustrate various aspects of the present invention. They are not to be construed to limit the claims in any manner whatsoever.

EXAMPLES 1-2

Determining the Solubility of Zein

The approximate solubilities of zein in different ethanol: water and acetone:water (v/v) mixtures are determined. In Example 1, dehydrated ethanol USP obtained from a commercially available source (Midwest Grain Products Co., Pekin, Ill.) is added in different proportions (0/10, 2/8, 4/6, 5/5, 6/4, 7/3, 8/2, 9/1, 10/0) to water. Next, a commercially available zein-granular powder (Freeman Industries, Inc. Tuckahoe, N.Y.) is added to 10 ml of each of the solvent mixtures in a glass vial. The mixtures are then agitated in a horizontal shaker. The solubility (w/v) is then determined. The results are set forth in Table 1 below.

Example 2 is prepared in similar fashion to Example 1, with acetone from a commercially available source (Mallinckrodt Inc., Paris, Ky.) being substituted for the ethanol. The results are similar to those set forth for Example 1.

TABLE 1

| Ingredient | Solubility of Zein in Ethanol/Water Mixtures | | | | | | | | |
|---|---|---|---|---|---|---|---|---|---|
| | Amount | | | | | | | | |
| ethanol/water (v/v) | 0/10 | 2/8 | 4/6 | 5/5 | 6/4 | 7/3 | 8/2 | 9/1 | 10/0 |
| zein (g in 10 ml) | 0.20 | 0.20 | 0.20 | 1.0 | 0.40 | 4.00 | 4.00 | 4.00 | 0.20 |
| solubility (w/v) | <0.1% | <2% | <2% | ≈10% | ≈40% | ≈40% | ≈40% | ≈40% | <0.1% |

As can be seen from the results set forth in Table 1, more than 40% w/v zein can be dissolved in solvent mixtures with a volume percentage of ethanol or acetone between 60 and 90. The viscosity of these concentrated solutions is high.

EXAMPLES 3-5

Preparation of Aqueous

Dispersion of Zein - Precipitation Method

In Example 3, solutions of zein in ethanol/water or acetone/water are added into an aqueous phase under continuous stirring. In Example 3, the solvent mixture used is ethanol:water (8:2 v/v), whereas in Example 4 the solvent mixture used is acetone:water (8:2 v/v).

In Examples 3-4, 200 ml of the solvent mixture (ethanol/water and acetone/water, each in a ratio of 8:2 v/v, respectively) is prepared, and then 10% w/v zein is added. The resultant zein solution is poured as a thin stream into 200 ml water. The zein precipitates immediately as fine particles resulting in dispersions. Stirring is continued to evaporate the organic solvent and concentrate the aqueous phase, the alcohol and some water are evaporated off at room temperature to provide an aqueous dispersion of zein (e.g., 6-10% w/v zein, and preferably 6-8% zein).

The average particle size of the zein latex obtained by the evaporative method is from about 240 nm to about 300 nm, as determined by photon correlation spectroscopy (BI-200SM goniometer, BI-2030 digital correlator, Melles Griot 10 mW He-Ne laser, Brookhaven Instruments Corporation, Holtsville, N.Y.). Latexes are formed at zein concentrations of 6% w/v and 3% w/v.

In Example 5, zein dispersions are prepared by dissolving zein in ethanol/water (6/4, v/v). The resulting solution is poured onto an agitated aqueous phase. Zein precipitates as fine particles resulting in dispersions. These dispersions are then concentrated.

Further investigations considered formulation variables such as the zein concentration, the volume of the zein solution, the volume of the external aqueous phase, and the addition of surfactants. From the results obtained, it was determined that the upper limit of zein concentration in the aqueous zein dispersions is about 10% w/v; higher concentrations of zein result in lump formation. Moreover, after concentrating the dispersions, the maximum solids content obtainable by this method is about 8% w/v.

EXAMPLES 6-7

Preparation of Aqueous Dispersion of Zein - Evaporation Method

In Example 6, zein is added to solvent mixtures comprising ethanol/water and acetone/water (8:2 v/v). The resultant zein solutions are placed in a beaker and stirred with a magnetic stirrer.

In Example 6, the zein precipitates from solution after evaporation of the organic solvent until a zein concentration of 30% w/v is obtained. The product obtained in Example 6 did not have a pseudolatex formation, and large agglomerates/viscous lumps formed.

In Example 7, the organic solvent is evaporated over a period of 48 hours in a one liter beaker, and a zein concentration of 3% w/v is obtained. The pH range of the product was 5-7. The product of Example 7 did have pseudolatex formation. However, in addition to small nanoparticles, some larger lumps and agglomerates were formed.

The results indicate that the precipitation method is superior to the evaporation method. Table 2 below is ia comparison of results obtained by these two methods.

TABLE 2

| Comparison of Results Obtained by Evaporation and Precipitation Methods | | | |
|---|---|---|---|
| | Evaporation | | Precipitation |
| Zein conc. (% w/v) | 30 | 3 | 6 | 3 |
| Pseudolatex formation (Y/N) | N | Y* | Y | Y |

*Dispersion agglomerated

EXAMPLES 8-9

Redispersibility of Zein Particles

In Examples 8-9, zein latexes prepared according to Example 4 are spray-dried using a Buchi Mini Spray dryer (Model 190, Brinkmann Instruments, Inc., Westbury, N.Y.; inlet temperature=90° C.). In Example 8, a 5% w/v zein solution was prepared in acetone/water (7/3 v/v). In Example 9, a 10% w/v zein solution was prepared in ethanol/water (6/4 v/v).

In each of Examples 8 and 9, fine zein particles smaller than about 10 μm are obtained. Most of the zein particles are smaller than about 5 μm.

EXAMPLE 10

Effect of pH Changes

In Examples 10a-d, zein pseudolatexes are prepared according to Example 4. A solvent mixture of ethanol and water (6/4) is prepared, and 6% zein w/v is added. 20 ml of the mixture is then added to an external aqueous phase.

In Example 10a, the external aqueous phase comprises a 20 ml buffer solution prepared according to USP at different pH. The different buffer solutions and results are set forth in Table 3. From these results, it is concluded that a dispersion of zein can be formed in buffers of high pH.

TABLE 3

| Stirring time | pH 1.1 | pH 3 | pH 5 | pH 7.4 | pH 9 | pH 10 |
|---|---|---|---|---|---|---|
| 0 | large aggregates | | aggregates | | pseudolatex & little aggregates | |
| overnight | large aggregates | | aggregates | | pseudolatex & little aggregates | | pH 1.1: 0.1 M HCl
pH 3: 0.2 M potassium hydrogen phthalate and 0.2 M HCl
pH 5: 0.2 M potassium biphthalate and 0.2 M NaOH
pH 7.4: 0.2 M monobasic potassium phosphate and 0.2 M NaOH
pH 9 and pH 10: 0.2 M boric acid + potassium chloride and 0.2 M NaOH In Example 10b, the external aqueous phase comprises a 20 ml buffer solution prepared according to USP of 0.1 M citric acid and 0.2 M $Na_2HPO_4$ at pH 3.5, pH 5, and pH 7.4. At each pH, aggregates form when the zein solution is added.

In Example 10c, the external aqueous phase comprises a 20 ml solution with a pH 7.4 buffer with different ionic strengths using NaCl to adjust ionic strength to 0.144, 0.25, 0.5, 0.75 and 1.0. At each of these ionic strengths, large aggregates form when the zein solution is added.

In Example 10d, the external aqueous phase comprises a 20 ml solution with a pH 9.5 buffer made from ammonium carbonate-ammonia. An acceptable pseudolatex is produced after stirring overnight.

EXAMPLE 11

Zein Film Coatings

In Example 11, a zein pseudolatex is prepared according to the procedure set forth in Example 4. The solid content of the latex is 5% zein (w/v). The zein pseudolatex is then plasticized by adding 20% propylene glycol, based on the zein content. Thereafter, the zein latex is applied as a coating onto substrates.

In Example 11a, Nu-pareil beads are loaded with chlorpheniramine maleate, and thereafter coated with the zein latex in a Uni-Glatt fluidized bed coater equipped with a Wurster column. An inlet temperature of 60° C. is used. An approximate 10% weight gain is applied to the beads. The pseudolatex is found to be easy to use and does not contain any undispersed zein. No sticking or congealing is noted.

While the zein pseudolatex as prepared above was useful as a coating, it did not provide a slow release of the chlorpheniramine maleate from the zein coated beads (the drug was released at the same rate as the uncoated beads). Examination using scanning electron microscopy revealed numerous cracks in the film coat.

In Example 11b, DSC analysis was performed on the zein latex film samples that were cast at room temperature and at 60° C. The Tg of the room temperature sample was 327° K and the Tg of the 60° C. film sample was 370° K, indicating that the film formed at the lower temperature was plasticized to a greater degree, possibly due to residual moisture in the film and the loss of the propylene glycol at 60° C.

In Example 11c, a second batch of zein latex (5% solid) is used to coat chlorpheniramine maleate-loaded beads under different operating conditions, with an inlet temperature of 35° C. The results of Example 11c were similar to those of Examples 11a and 11b, with scanning electron microscopy revealing numerous cracks in the coating.

In Example 11d, further studies are conducted to determine the effect of increasing amounts of plasticizer in the aqueous zein dispersion, and to determine the effect of relative humidity. A zein film containing equal amounts of propylene glycol and zein on a weight basis is determined to be flexible at about 0% relative humidity, but becomes very sticky at 50% relative humidity. For a zein film containing 35% propylene glycol on a weight basis of zein, at 50% relative humidity the film remains flexible. At higher relative humidities, the film becomes more sticky, and at lower relative humidities it slowly becomes more brittle as the film dried and moisture is lost from the film. From these studies, it is concluded that a propylene glycol range of about 10-40% would be suitable, with a propylene glycol range of 20-25% being most preferred.

EXAMPLE 12

Preparation of Zein Films

In Example 12, zein solutions are prepared with and without plasticizer, and cast into aluminum petri dishes and dried at room temperature. In each of Examples 12a-12, the zein is added to 5-7 ml of a solvent mixture of ethanol/water (Examples 12a and 12b) or acetone/water (Examples 12c and 12d) in a ratio of 8:2 v/v. In Examples 12a and 12c, the resultant solution comprises 20% zein w/v; in Examples 12b and 12d the resultant solution comprises 30% zein w/v. Propylene glycol 20-40% is incorporated into the solutions as a plasticizer prior to casting. Smooth, transparent, flexible films are formed from 25% or 30% w/v zein solutions in ethanol or acetone/water mixtures (8:2 v/v). ! However, the films became brittle after a few days and after storage of the films in a desiccator, possibly due to further water evaporation or evaporation of the propylene glycol. In order to improve the flexibility of the film, different plasticizers are added to the polymer solution. The results indicate that water-soluble plasticizers, e.g., glycerin, propylene glycol, and PEG 400, provide flexible films when compared to the water-insoluble plasticizers, e.g., dibutyl sebacate (DBS), triethyl citrate (TEC), tributyl citrate (TBC), acetyltributyl citrate (ATBC), and acetyltriethyl citrate (ATEC). Propylene glycol at a concentration from about 20 to about 25%, based on the amount of zein, appears to be the best plasticizer of those studied.

EXAMPLES 13-18

Stabilizing Aqueous Zein Dispersions With Different Preservatives

In Examples 13-18, different preservatives are added to zein dispersions made according to the present invention, and the effect of the preservative on the zein dispersion was noted upon storage. For each of Examples 13-18, the zein dispersion is prepared in accordance with Example 3, i e., 6% zein in ETOH/water solution (6/4, 10 ml) was added to the same amount of water to make the zein dispersion. Thereafter, the preservatives Were added and the dispersion was continuously stirred for two days.

In Example 13, the preservative is benzalkonium chloride 0.25% w/v. In Example 14, the preservative is benzoic acid 0.5% w/v. In Example 15, the preservative is sodium benzoate 0.5% w/v. In Example 16, the preservative is benzyl alcohol 1% w/v. In Example 17, the preservative is methyl paraben, 0.2% w/v. In Example 18, the preservative is propyl paraben, 0.02% w/v. The zein dispersions of Examples 13-18, along with a control (zein dispersion without preservative) were then stored at room temperature for 5 days, and then examined at 0 days, 2 days, 5 days, 15 days, 30 days, 45 days and 90 days. The results are set forth in Table 4:

benzoate, an anionic preservative, resulted in rapid aggregation, possibly suggesting a positive charge of the zein particles. The other preservatives (benzalkonium chloride, benzoic acid, benzyl alcohol, methyl paraben and propyl paraben) significantly improved the stability when compared to a preservative-free dispersion which sedimented an unpleasant odor after approximately one week.

TABLE 4

Examples 13-18
Effect Of Preservatives On The
Preparation Of Zein Dispersions

| Preservative | Amount %, w/v | Solid Content % | 0 days | Storage Time 2 days | 5 days* | 15 days | 30 days | 45 days | 90 days |
|---|---|---|---|---|---|---|---|---|---|
| Benzalkonium chloride | 0.25 | 6.3 | good | good | good | unchanged | 10% sediment | unchanged | 20% sediment |
| Benzoic acid | 0.5 | 6.35 | good | good | good | unchanged | 2.5% sediment | unchanged | 10% sediment |
| Sodium benzoate | 0.5 | rapid aggregation and sediment | — | — | — | — | — | — | — |
| Benzyl alcohol | 1 | 5.95 | good | good | good | unchanged | 1% sediment | unchanged | 8% sediment |
| Methyl paraben | 0.2 | 5.55 | good | good | good | unchanged | unchanged | unchanged | 4% sediment |
| Propyl paraben | 0.02 | 5.05 | good | good | good | unchanged | unchanged | unchanged | 4% sediment |
| control | 0 | 5.6 | good | good | good | all sediment | bad smell | bad | bad |

*5 days later, all samples had a little sediment.

EXAMPLES 19-12

In Examples 19-23, plasticizers, triethyl citrate (TEC) 20% w/v and propylene glycol (PG) 20% w/v were added to the zein dispersions along with a preservative. In Example 19, the preservative was benzalkonium chloride 0.25% w/v. In Example 20, the preservative was benzoic acid 0.5% w/v. In Example 21, the preservative was sodium benzoate 1% w/v. In Example 22, the preservative was methyl paraben 0.2% w/v. In Example 23, the preservative was propyl paraben 0.02% w/v. The plasticized zein dispersions of Examples 19-23 were then stored at room temperature along with a control sample (zein dispersions without plasticizer or preservative) for 13 days, and examined at 0 days, 4 days, 6 days, 10 days and 13 days. The results are set forth in Table 5 below:

The results indicate that only very little sedimentation was observed with the preserved dispersions and that the preservatives provide a stabilizing effect upon the aqueous zein dispersion.

EXAMPLES 24-28

Casting Films From Preserved Zein Dispersions

In Examples 24-28 the effect of different preservatives on the zein films and casting conditions are studied. In each of Examples 24-28, a zein dispersion is prepared in accordance with Example 4 (10 ml, 6.25% solids) and plasticized and a preservative added, with 20% triethyl citrate and 20% propylene glycol. In Example 24, the preservative is benzalkonium chloride 0.25% w/v. In Example 25 the preservative was benzoic acid 0.5% w/v. In Example 26, the preservative was sodium benzoate 1% w/v. In Example 27, the pre-

TABLE 5

Examples 19-23
Effect Of Preservatives On
The Storage Of Zein Dispersions

| Preservative | Amount %, w/v | Storage Time | | | | |
|---|---|---|---|---|---|---|
| | | 0 days | 4 days | 6 days | 10 days | 13 days |
| Benzalkonium chloride | 0.25 | good | good | good | good | very little sediment |
| Benzoic acid | 0.5 | good | good | good | bad smell | little sediment |
| Sodium benzoate | 0.5 | rapid aggregation and sediment | — | — | — | — |
| Benzyl alcohol | 1 | good | good | good | good | very little sediment |
| Methyl paraben | 0.2 | good | good | good | little sediment | unchanged |
| Propyl paraben | 0.2 | good | good | good | little sediment | unchanged |
| Control | 0 | good | good | some sediment | bad smell and sediment | all sedimented |

The results for the unplasticized zein dispersions (Examples 13-18) and the plasticized zein dispersion (Examples 19-23) were similar. The addition of sodium servative was methyl paraben 0.2% w/v. In Example 28, the preservative was propyl paraben 0.02% w/v. Zein films are then cast from the zein dispersions of Examples 24-28 and then for each Example, the zein films are dried at 60° C. overnight and at room temperature for three days. The results are provided in Table 6 below:

TABLE 6

Effect Of Different Preservatives On The Zein Films

| Preservative | Amount %, w/v | 60° C. | Room Temperature |
|---|---|---|---|
| Benzalkonium chloride | 0.25 | brittle, clear | flexible, clear |
| Benzoic acid | 0.5 | brittle, clear | flexible, clear |
| Sodium benzoate | 0.5 (rapid aggregation) | brittle, cloudy | flexible, clear |
| Benzyl alcohol | 1 | brittle, clear | flexible, clear |
| Methyl paraben | 0.2 | brittle, clear | flexible, clear |
| Propyl paraben | 0.02 | brittle, cloudy | flexible, cloudy |
| control | 0 | brittle, cloudy | flexible, cloudy |

As can be ascertained from the results reported in Table 6, all of the zein films were clear and flexible when stored at room temperature, except for propyl paraben. A plasticizing effect of the parabens could not be detected by this method when compared to preservative-free films.

EXAMPLES 29-32

Theophylline Tablets

In Examples 29-32, four different aqueous dispersions of zein prepared in accordance with Example 3 are applied to directly compressible theophylline tablets. The theophylline tablets each weight 300 mg, have a hardness of 9.5 kg, and have the ingredients set forth in Table 7 below:

TABLE 7

Theophylline Tablets

| Ingredients | Amount |
|---|---|
| Theophylline Granules | 225 mg |
| Fast Flow Lactose #316 | 73.5 mg |
| Magnesium Stearate | 1.5 mg |
| Total Weight | 300 mg |

The theophylline tablets are prepared by compressing a granulation of the theophylline granules, lactose and magnesium stearate on a stokes rotary press into tablets weighing 300 mg. When tested in-vitro, the tablets release theophylline over a period of 30 minutes. In Example 29, the theophylline tablets are coated with a zein pseudolatex dispersion including benzoic acid as a preservative and having the ingredients set forth in Table 8 below:

TABLE 8

Example 29 - Benzoic Acid

| Ingredients | Amount |
|---|---|
| Zein | 18 g |
| Benzoic Acid | 1.8 g |
| Final Volume of Latex | 360 ml |
| Propylene Glycol | 25% (of solids) |
| Solids content | 5% |

In Example 30, the theophylline tablets are coated with a zein pseudolatex dispersion having benzalkonium HCl as a preservative, as in Table 9 below:

TABLE 9

Example 30 - Benzalkonium HCl

| Ingredients | Amount |
|---|---|
| Zein | 18 g |
| Benzalkonium HCl | 0.9 g |
| Final Volume of Latex | 340 ml |
| Propylene Glycol | 25% (of solids) |
| Solids Content | 5.35% |

In Example 31, the theophylline tablets are coated with a zein pseudolatex dispersion having methyl paraben and propyl paraben as preservatives, and also include lactose as set forth in Table 10 below:

TABLE 10

Example 31 - Parabens and Lactose

| Ingredients | Amount |
|---|---|
| Zein | 18 g |
| Lactose | 2.0 g |
| Propyl Paraben | 0.02% |
| Methyl Paraben | 0.2% |
| Propylene Glycol | 25% (of solids) |
| Solids Contents | 5.67% |

In Example 32, the theophylline tablets are coated with a zein pseudolatex dispersion having methyl and propyl paraben as preservatives, and further include hydroxypropylmethylcellulose (HPMC), as set forth in Table 11 below:

TABLE 11

Example 32 - Parabens and HPMC

| Ingredients | Amount |
|---|---|
| Zein | 18 g |
| HPMC | 2.0 g |
| Propyl Paraben | 0.02% |
| Methyl Paraben | 0.2% |
| Propylene Glycol | 25% (of solids) |
| Solids Contents | 5.59% |

In each of Examples 29-32, the theophylline tablets are coated using a Hi-Coater at an inlet temperature of 60° C., an outlet temperature of 28° C., and a pan rotation speed of 20 rpm. The coated tablets are then cured for 24 hours in a 40° C. oven.

The cured coated theophylline tablets of Examples 29-32 are then subjected to dissolution testing according to USP method II in 900 ml deionized water maintained at 37° C.

FIG. 1 shows the dissolution results of Examples 29 and 30 as compared to uncoated theophylline tablets.

The dissolution profiles in FIG. 1 indicate that zein with benzoic acid (Example 29) provides no release of theophylline within an 8 hour time span, and that the zein with benzalkonium HCl (Example 30) provides a slow incremental release of theophylline from 0% to 6% in the span of 8 hours. In comparison, the uncoated theophylline tablets release substantially all of the theophylline within one hour. The results provided in FIG. 1 show that the drug release from the zein-coated tablets is effectively closed down.

Figure 2:
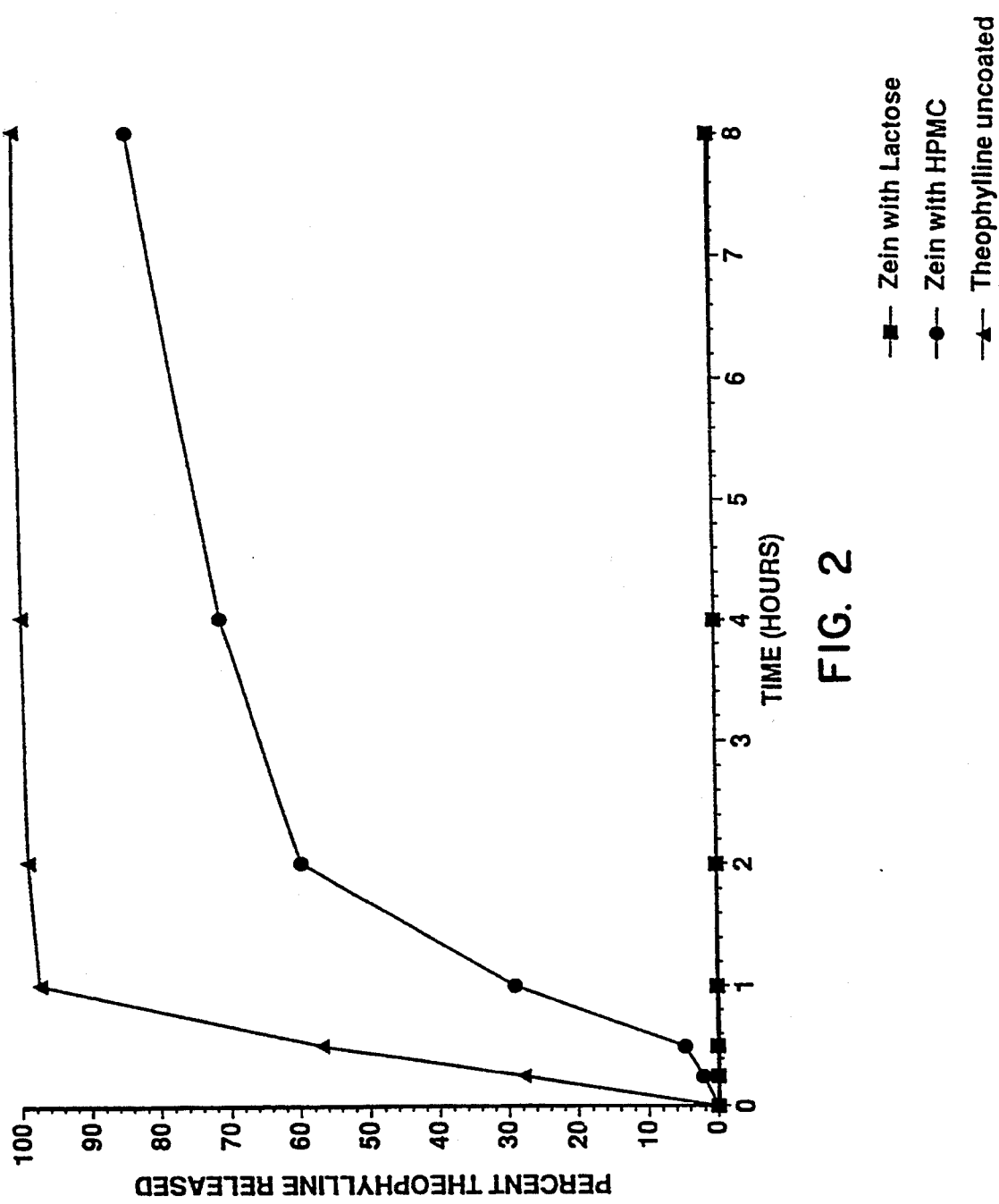
FIG. 2 is a graphical representation of the dissolution profiles obtained by Example 31.

A similar result as illustrated in FIG. 2 is obtained with zein dispersions containing lactose and parabens (Example 31). Similar to Example 29, no theophylline is released from the tablets of Example 31 (zein dispersion with lactose and methyl and propyl paraben). Zein with lactose shows no release within the span of 8 hours.

The inclusion of HPMC in the zein/methyl and propyl paraben dispersion (Example 32) results in an increase in drug release rate over time, and the HPMC increases the permeability of the film coat as indicated by the drug release profile shown in FIG. 2.

The results indicate that parabens and benzoic acid play a significant role in the preservation of the zein dispersions of the present invention.

EXAMPLES 33-36

Zein Coating Applied To APAP Tablets

A zein pseudolatex (6.1% solids) is prepared in accordance with Example 3, and preserved with a combination of propyl and methyl paraben (0.02% and 0.2% w/v, respectively). The preserved pseudolatex is plasticized with 25% w/v propylene glycol and stirred gently for four hours.

APAP tablets are prepared by compressing Compap Coarse L (90% acetaminophen) commercially available from Mallinckrodt, Inc. to a weight of 500 mg.

The plasticized latex was applied to 300 mg acetaminophen (APAP) tablets in a Hi-Coater, inlet temperature 60° C., outlet 28° C., pan rotation speed maintained at 20 rpm.

In Example 33, the APAP tablets are coated to a weight gain of 0.67%. In Example 34, the APAP tablets are coated to a weight gain of 2.67%. In Example 35, the APAP tablets are coated to a weight gain of 5.29%. In Example 36, the APAP tablets are coated to a weight gain of 7.64%. Samples are taken at regular intervals and percent weight gain is determined. All samples are then allowed to cure in a 40° C. oven for 24 hours.

Figure 3:
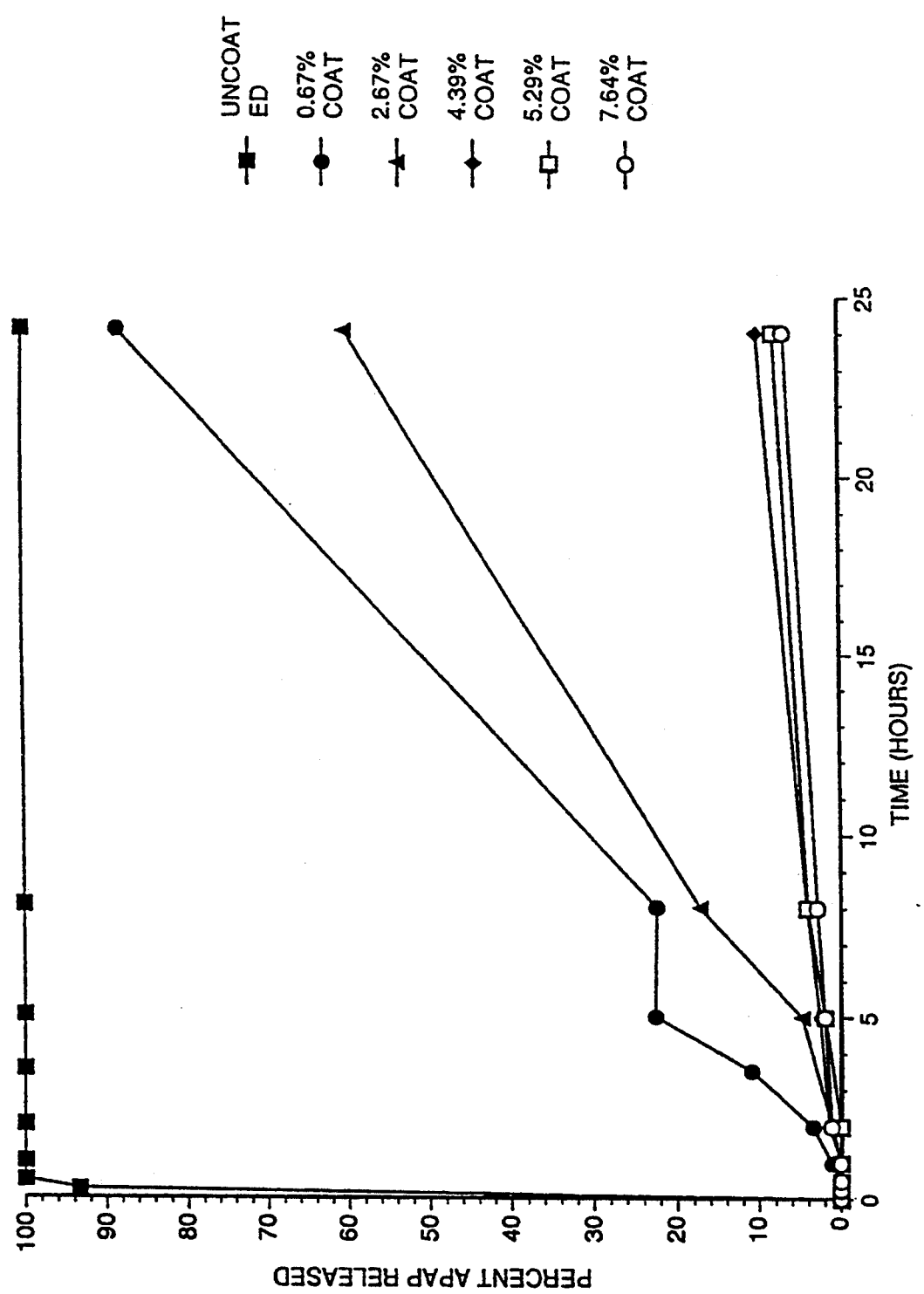
FIG. 3 is a graphical representation of the dissolution profiles obtained by Examples 33-36.

Next, the dissolution of the coated APAP tablets of Examples 33-36 (3 samples of each) is tested in 0.1 N HCl, deionized (DI) water, and 0.1 N phosphate buffer at 37° C., in accordance with USP Method II. As a control, the dissolution of uncoated APAP tablets is also examined. The results are provided in FIG. 3. The dissolution data provided in FIG. 3 indicate that by increasing the percentage of the coating on the APAP tablets, the release of the APAP was reduced.

EXAMPLES 37-39

Figure 4:
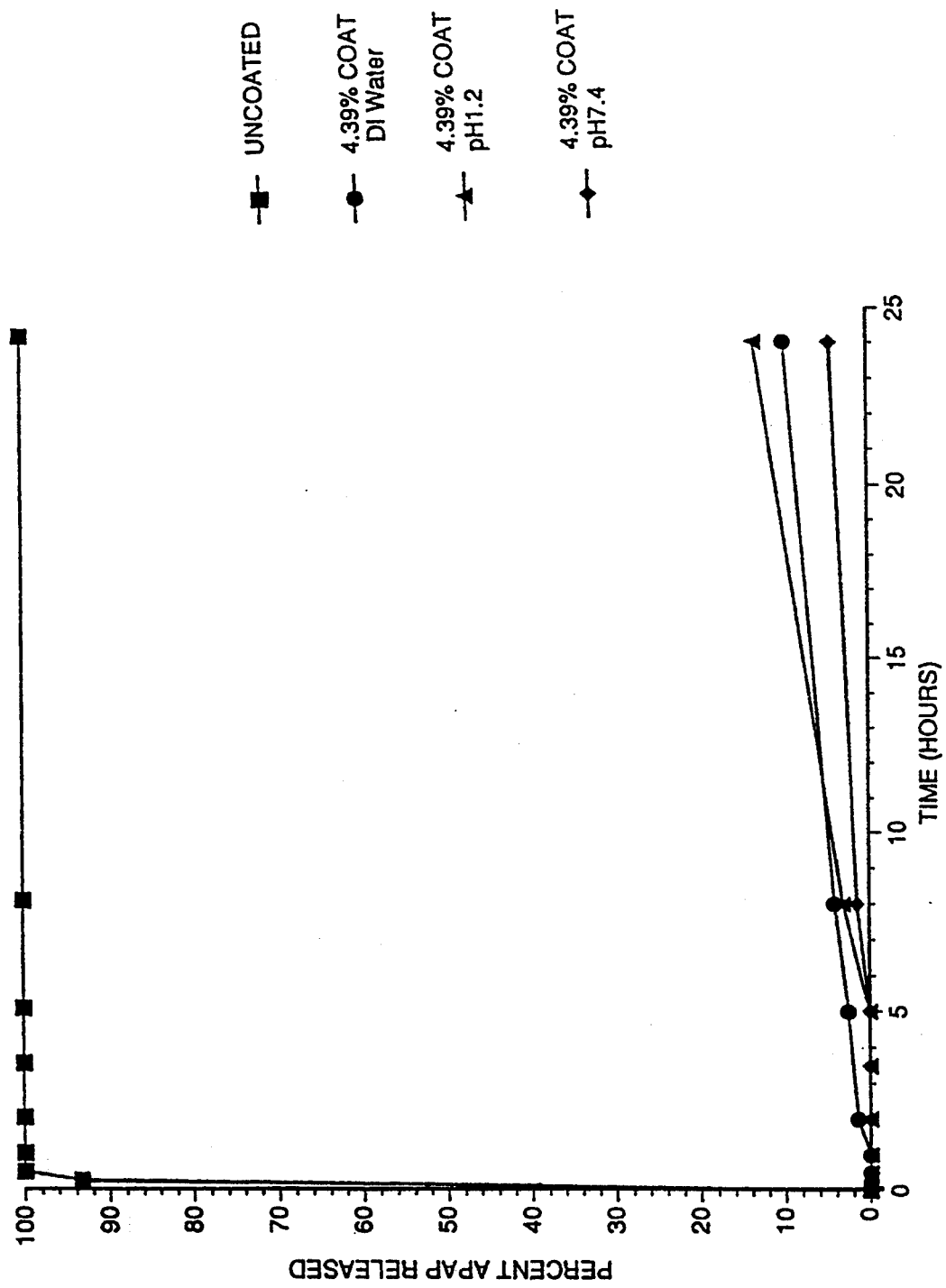
FIG. 4 is a graphical representation of the dissolution profiles obtained by Examples 37-39.

In Examples 37-39, the effect of 0.1 N HCl (pH 1.02), and 0.1 N Phosphate buffer (pH 7.4) on the release of APAP from zein-coated APAP tablets prepared in accordance with Examples 33-36 and coated to a weight increase of 4.39% is investigated. The dissolution results are reported in FIG. 4. The results indicate a negligible effect on release of the APAP due to the pH of the dissolution media. The tablets are tested for dissolution in 0.1 N HCl (pH=1.2; Example 37); 0.1 N phosphate buffer (pH=7.4; Example 38) and deionized water (Example 39).

EXAMPLES 40-42

Different Concentrations of Paraben

In Examples 40-42, the effect of varying the amount of methyl paraben incorporated in the zein pseudo-latex on the release of APAP from coated APAP tablets is investigated.

In each of Examples 40-42, APAP tablets prepared in accordance with Examples 33-36 are coated with zein pseudo-latex plasticized with propylene glycol (25% w/v). In Example 40, preservative is 0.02% propyl paraben (no methyl paraben included). In Example 41, the preservative is 0.05% methyl paraben and 0.02% propyl paraben. In Example 42, the preservative is 0.2% methyl paraben and 0.02% propyl paraben. The coated tablets of Examples 40-42 and a control (uncased APAP tablet) are then subjected to dissolution testing in accordance with USP Method II in deionized water at 37° C. The results are set forth in FIG. 5.

Figure 5:
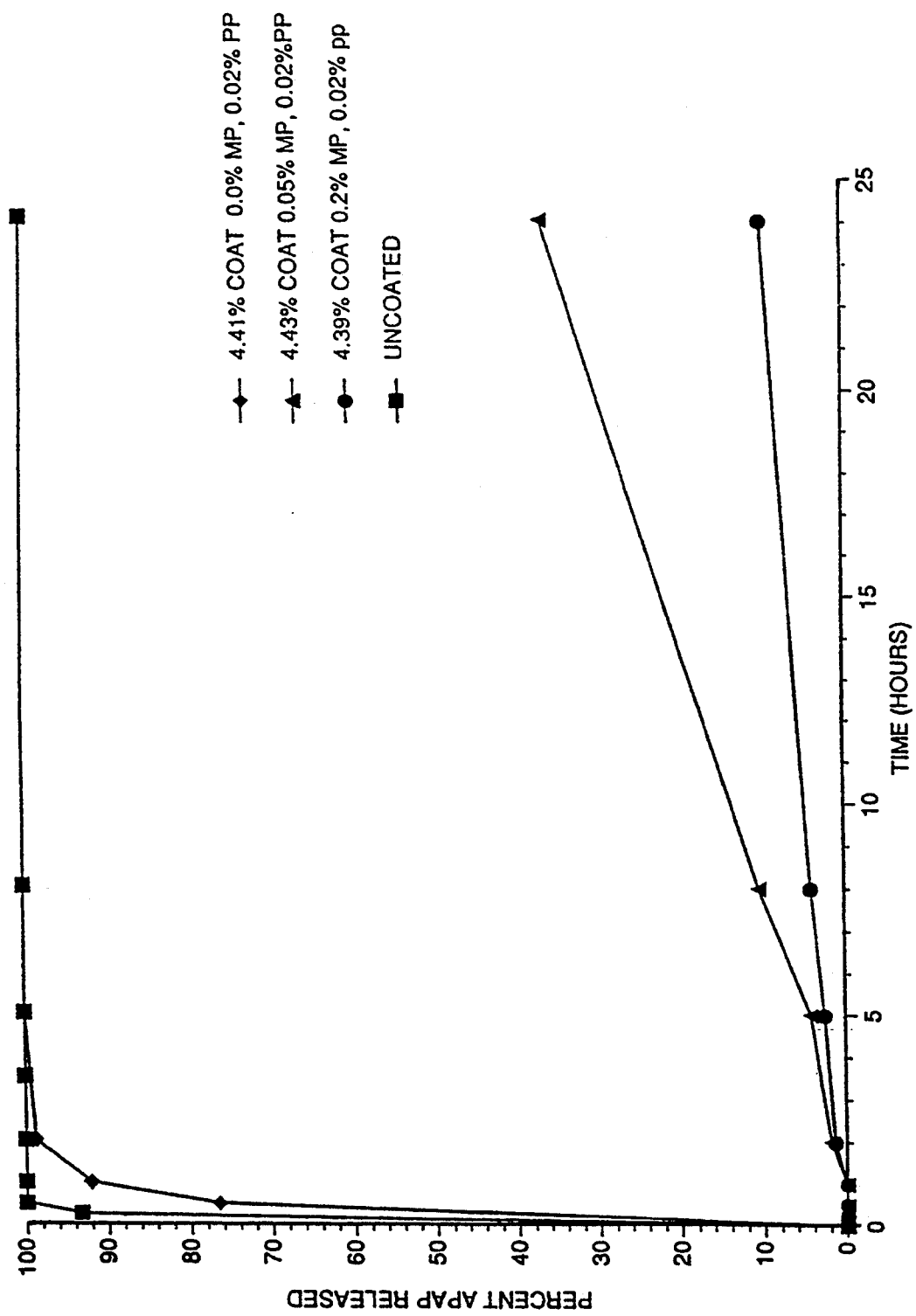
FIG. 5 is a graphical representation of the dissolution profiles obtained by Examples 40-42.

As indicated by FIG. 5, the tablets containing no methyl paraben dose-dump very quickly due to failure of the film coat. Inspection of these tablets reveals numerous small cracks in the coating which allow rapid hydration of the tablet core. The addition of methyl paraben at a 0.05% level substantially improved the coating. The release of APAP is virtually shut down at 0.2% concentration of methyl paraben.

EXAMPLES 43-45

Effect of Different Temperatures on Aged Zein Latex

In Example 43, a zein pseudolatex (6.1% solids) is prepared in accordance with Example 3 and is preserved with a combination of propyl and methyl paraben at concentrations of 0.02% and 0.2%, respectively. A portion of the preserved zein pseudolatex equivalent to 15 g solids was plasticized with 25% propylene glycol and stirred gently for 24 hours. The plasticized zein pseudolatex is then applied to APAP tablets in accordance with Examples 33-36 to a 5% weight gain. The remaining portions of the preserved zein pseudolatex is divided into two lots and stored at room temperature and at 4° C., respectively, for a two week period. The stored zein pseudolatex is then plasticized with propylene glycol 25% and is sprayed onto APAP tablets in the same manner to a 5% weight gain. In Example 44, the tablets coated with the aged zein pseudolatex are held at room temperature for two weeks. In Example 45, the aged zein pseudolatex is held at 40° C. for two weeks.

Figure 6:
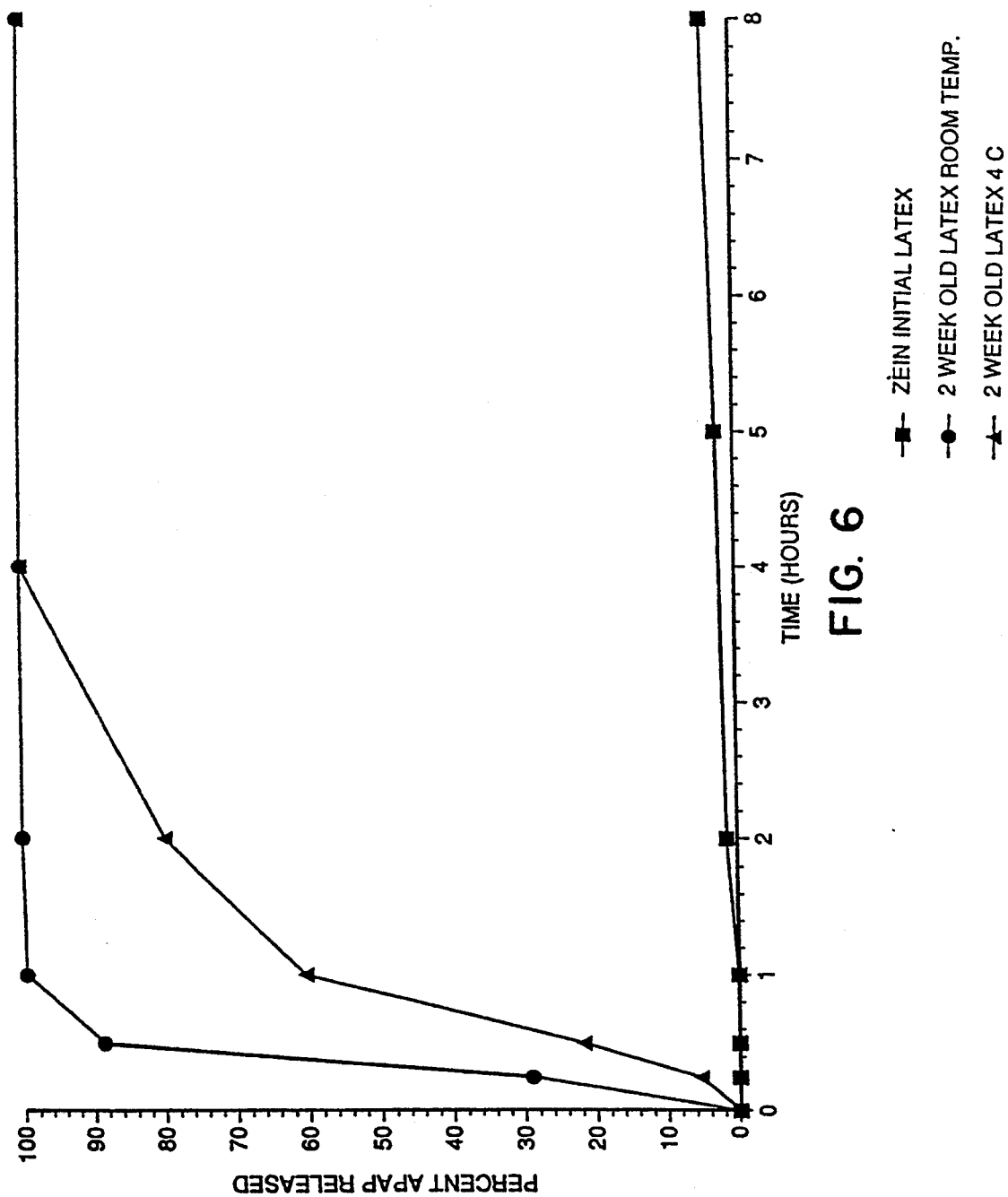
FIG. 6 is a graphical representation of the dissolution profiles obtained by Examples 44 and 45.

Thereafter, dissolution tests are performed on the tablets of Examples 44-45 in 900 ml deionized water at 37° C., the results of which are provided in FIG. 6. The results indicate that the tablets coated with the aged zein pseudolatex (Examples 44 and 45) displayed surface cracks and imperfections, as compared to the smooth, continuous surface of tablets coated with fresh zein pseudolatex (Example 43), which is 5 days old at the time of spraying. This 5 day time period is necessary for the evaporation of the water and alcohol to concentrate the dispersion to the 6.1% solids level.

Figure 7:
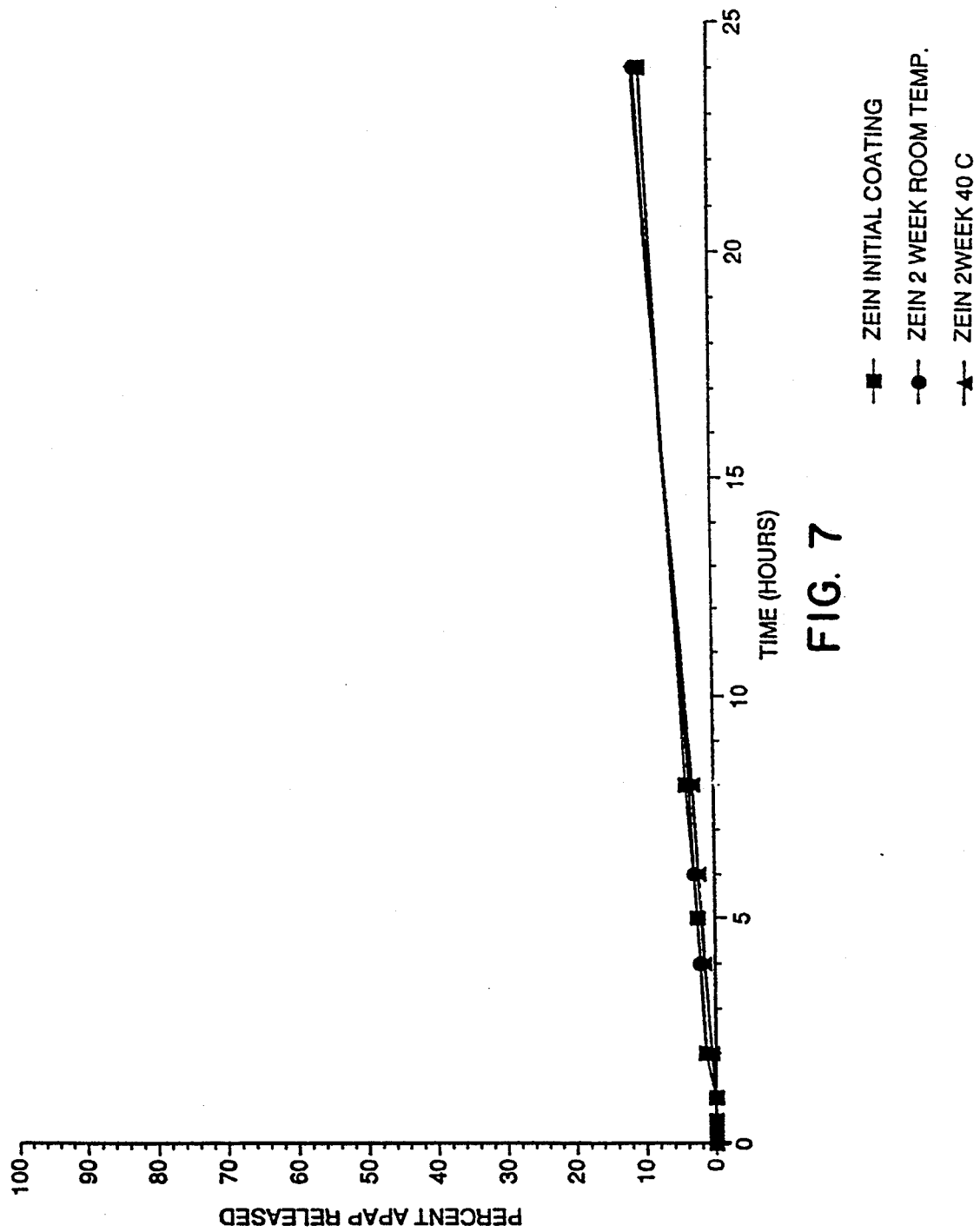
FIG. 7 is a graphical representation of the dissolution profiles obtained by Example 43.

Next, the tablets of Example 43 are placed in closed containers and held for two weeks at room temperature and at 40° C. Dissolution tests are performed and the results show no differences in the release profile, as shown in FIG. 7.

EXAMPLES 46-47

Addition of a Pore-Former

Figure 8:
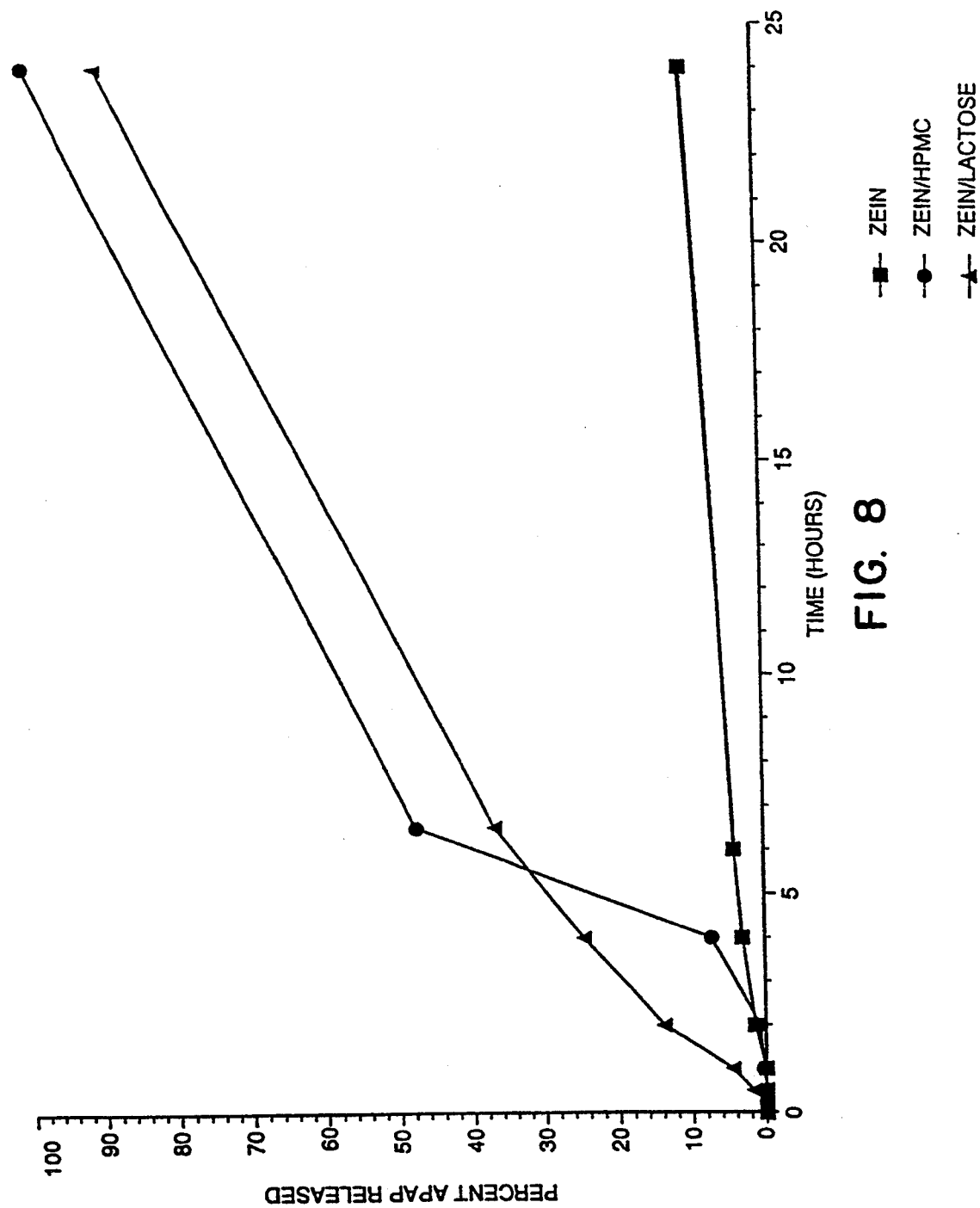
FIG. 8 is a graphical representation of the dissolution profiles obtained by Examples 46 and 47.

In Example 46, two batches of zein pseudolatex are prepared (16 g solids each) in accordance with Example 43. Two grams of hydroxypropylmethylcellulose (HPMC) is added to one batch (Example 46) and two grams of lactose is added to the other (Example 47). The zein pseudolatexes of Examples 46 and 47 are then plasticized, preserved with polyethylene glycol (25% w/v); methyl paraben (0.2% w/v); and propyl paraben (0.02$ w/v); and sprayed onto APAP tablets to a weight gain of 5%. Dissolution tests are performed in 900 ml of deionized water at 37° C. The results are shown in FIG. 8.

The results indicate that drug release profiles can be regulated with the use of pore-forming materials in the zein pseudolatexes of the present invention. The APAP tablets used in this study tended to swell and disintegrate rapidly. The zein pseudolatex formations that include pore-forming materials would be more suited to a non-disintegrating tablet formation, where the drug release would ideally be diffusion-controlled.

The examples provided above are not meant to be exclusive. Many other variations of the present invention would be obvious to those skilled in the art, and are contemplated to be within the scope of the appended claims.

What is claimed is:

1. A stabilized aqueous dispersion of zein, comprising
   an aqueous dispersion comprising from about 0.1 to about 10 percent zein w/v having a particle size from about 0.01 $\mu$m to about 10 $\mu$m, and
   an amount effective to preserve said dispersion of a pharmaceutically acceptable preservative.

2. The stabilized aqueous dispersion of claim 1, wherein said pharmaceutically acceptable preservative is selected from the group consisting of benzalkonium chloride, benzoic acid, benzyl alcohol, methyl paraben, propyl paraben, ethyl paraben, butyl paraben, sorbic acid, a quaternary ammonium salt, phenol, cresol, mercury-containing preservatives, and mixtures of any of the foregoing.

3. The stabilized aqueous dispersion of claim 1, wherein said pharmaceutically acceptable preservative is selected from the group consisting of benzalkonium chloride, benzoic acid, methyl paraben, propyl paraben, and mixtures thereof.

4. The stabilized aqueous dispersion of claim 1, wherein said pharmaceutically acceptable preservative comprises methyl paraben in an amount of at least 0.05%, w/v.

5. The stabilized aqueous dispersion of claim 1, wherein said pharmaceutically acceptable preservative comprises about 0.2% methyl paraben and 0.02% propyl paraben, w/v.

6. The stabilized aqueous dispersion of claim 1, comprising from about 3 to about 8 percent zein, w/v.

7. The stabilized aqueous dispersion of claim 1, further comprising an effective amount of water-soluble plasticizer to provide a flexible film when said aqueous dispersion is applied to a substrate.

8. The stabilized aqueous dispersion of claim 1, wherein said water-soluble plasticizer is selected from the group consisting of glycerin, propylene glycol, polyethylene glycol, triethyl citrate, and mixtures of any of the foregoing.

9. The stabilized aqueous dispersion of claim 1, which has less than 20% sedimentation after 30 days.

10. A method of preparing a stable aqueous dispersion of zein, comprising adding a pharmaceutically acceptable preservative to an aqueous dispersion of zein comprising from about 0.1 to about 10 percent zein w/v having a particle size from about 0.01 microns to about 10 microns.

11. The method of claim 10, wherein said pharmaceutically acceptable preservative is selected from the group consisting of benzalkonium chloride, benzoic acid, benzyl alcohol, methyl paraben, propyl paraben, ethyl paraben, butyl paraben, sorbic acid, a quaternary ammonium salt, phenol, cresol, mercury-containing preservatives, and mixtures of any of the foregoing.

12. The method of claim 10, wherein said pharmaceutically acceptable preservative is selected from the group consisting of benzalkonium chloride, benzoic acid, methyl paraben, propyl paraben, and mixtures thereof.

13. The method of claim 10, wherein said pharmaceutically acceptable preservative comprises methyl paraben and propyl paraben in a ratio of about 10:1, said methyl paraben being present in an amount of at least 0.05%, w/v.

14. The method of claim 10, wherein said pharmaceutically acceptable preservative comprises about 0.2% methyl paraben and 0.02% propyl paraben, w/v.

15. A method for preparing an aqueous dispersion of zein, comprising
   adding zein to a solvent mixture comprising water and from about 60 to about 90 percent of an organic solvent selected from the group consisting of ethanol, acetone, and mixtures thereof, such that the zein dissolves in the solvent mixture,
   precipitating the zein as fine particles by pouring said solution of zein as a thin stream into an aqueous phase under continuous stirring, to obtain an aqueous dispersion of zein comprising from about 0.1 to about 10 percent zein w/v,
   evaporating said organic solvent from the mixture, concentrating the resulting aqueous phase to a zein concentration up to about 10% w/v, and
   preserving the resulting aqueous dispersion of zein by adding an amount of effective to preserve said dispersion of a pharmaceutically acceptable preservative.

16. The method of claim 15, wherein said pharmaceutically acceptable preservative is selected from the group consisting of benzalkonium chloride, benzoic acid, benzyl alcohol, methyl paraben, propyl paraben, ethyl paraben, butyl paraben, sorbic acid, a quaternary ammonium salt, phenol, cresol, mercury-containing preservatives, and mixtures of any of the foregoing.

17. The method of claim 15, further comprising adding an effective amount of a pharmaceutically acceptable plasticizer to provide a flexible film, and thereafter applying said plasticized aqueous dispersion to a substrate.

18. The product produced by the method of claim 15.

19. A stabilized aqueous dispersion of zein, comprising
   an aqueous dispersion comprising from about 0.1 to about 10 percent zein w/v and having a particle size from about 0.01 $\mu$m to about 10 $\mu$m, said aqueous dispersion obtained by precipitating zein by pouring a solution of zein in a solvent comprising water and from about 60 to about 90 percent organic solvent as a thin stream into an aqueous phase under continuous stirring, the organic solvent thereafter being substantially removed and the resulting aqueous phase concentrated, and
   an amount effective to preserve said dispersion of a pharmaceutically acceptable preservative.

20. The stabilized aqueous dispersion of claim 19, wherein said organic solvent is selected from the group consisting of ethanol, acetone, and mixtures thereof.

21. The stabilized aqueous dispersion of claim 19, wherein said pharmaceutically acceptable preservative is selected from the group consisting of benzalkonium chloride, benzoic acid, benzyl alcohol, methyl paraben, propyl paraben, ethyl paraben, butyl paraben, sorbic acid, a quaternary ammonium salt, phenol, cresol, mercury-containing preservatives, and mixtures of any of the foregoing.

22. A solid controlled release formulation, comprising
- a substrate comprising an active agent, said substrate coated with a controlled release coating to a weight gain from about 3 to about 15 percent, said controlled release coating comprising
  - (i) an aqueous dispersion of from about 0.1 to about 10 percent zein w/v having a particle size from about 0.01 μm to about 10 μm, said aqueous dispersion obtained by precipitating zein by pouring a solution of zein in a solvent comprising water and from about 60 to about 90 percent organic solvent as a thin stream into an aqueous phase under continuous stirring, the organic solvent thereafter being substantially removed and the resulting aqueous phase concentrated;
  - (ii) a pharmaceutically acceptable preservative;
  - (iii) a pharmaceutically acceptable plasticizer, the preservative and the plasticizer each being included in an amount necessary to provide a strong, continuous film capable of releasing the active agent at a desired rate when the formulation is exposed to an aqueous solution.

23. The controlled release formulation of claim 22, wherein said organic solvent is selected from the group consisting of ethanol, acetone, and mixtures thereof and said pharmaceutically acceptable preservative is selected from the group consisting of benzalkonium chloride, benzoic acid, benzyl alcohol, methyl paraben, propyl paraben, ethyl paraben, butyl paraben, sorbic acid, a quaternary ammonium salt, phenol, creosol, mercury-containing preservatives, and mixtures of any of the foregoing.

24. The controlled release formulation of claim 23, wherein said controlled release coating further comprises a pore-former which is dissolved, extracted or leached from the coating in the environment of use.

25. The controlled release formulation of claim 23, wherein said coating further comprises one or more release-modifying passageways formed in said coating.

26. The controlled release formulation of claim 23 which is a tablet.

27. The controlled release formulation of claim 22, wherein said pharmaceutically acceptable preservative comprises methyl paraben in an amount of at least 0.05%, w/v.

28. The controlled release formulation of claim 22, wherein said plasticizer is selected from the group consisting of glycerin, propylene glycol, polyethylene glycol, triethyl citrate, and mixtures of any of the foregoing.

29. The controlled release formulation of claim 22, wherein said active agent is selected from the group consisting of a systemically active therapeutic agent, a locally active therapeutic agent, a disinfecting and sanitizing agent, a cleansing agent, a fragrance agent and a fertilizing agent.

30. The controlled release formulation of claim 22, wherein said therapeutically active agent is selected From the group consisting of antihistamines, analgesics, non-steroidal anti-inflammatory agents, gastro-intestinals, anti-emetics, anti-epileptics, vasodilators, anti-tussive agents, expectorants, anti-asthmatics, hormones, diuretics, anti-hypotensives, bronchodilators, steroids, antibiotics, antivirals, antihemorrhoidals, hypnotics, psychotropics, antidiarrheals, mucolytics, sedatives, decongestants, laxatives, vitamins, and stimulants.

31. A method for preparing a controlled release formulation comprising a substrate coated with an aqueous dispersion of zein, comprising
- adding zein to a solvent mixture comprising water and from about 60 to about 90 percent of an organic solvent selected from the group consisting of ethanol, acetone, and mixtures thereof, such that the zein dissolves in the solvent mixture,
- precipitating the zein as fine particles by pouring said solution of zein as a thin stream into an aqueous phase under continuous stirring, to obtain an aqueous dispersion of zein comprising from about 0.1 to about 10 percent zein w/v,
- evaporating said organic solvent from the mixture, concentrating the resulting aqueous phase to a zein concentration up to about 10% w/v,
- adding effective amounts of a pharmaceutically acceptable preservative and a plasticizer,
- coating a substrate comprising an active agent with a sufficient amount of the preserved, plasticized aqueous dispersion of zein to obtain a predetermined controlled release of said active agent when said coated substrate is exposed to fluid in an environment of use.

32. The method of claim 31, further comprising further controlling the release of said active agent by adding a pore-former which is dissolved, extracted or leached from the coating in the environment of use.

33. The method of claim 31, further comprising forming one or more release-modifying passageways in said coating.

34. The method of claim 31, wherein said water-soluble plasticizer is selected from the group consisting of glycerin, propylene glycol, polyethylene glycol, triethyl citrate, and mixtures of any of the foregoing.

* * * * *